(12) United States Patent
Blasio

(10) Patent No.: US 10,709,004 B2
(45) Date of Patent: Jul. 7, 2020

(54) OVERHEAD TUBE CRANE GUIDE

(71) Applicant: CARESTREAM HEALTH, INC., Rochester, NY (US)

(72) Inventor: Anthony J. Blasio, Honeoye Falls, NY (US)

(73) Assignee: Carestream Health, Inc., Rochester, NY (US)

( * ) Notice: Subject to any disclaimer, the term of this patent is extended or adjusted under 35 U.S.C. 154(b) by 192 days.

(21) Appl. No.: 15/967,963

(22) Filed: May 1, 2018

(65) Prior Publication Data

US 2018/0332695 A1 Nov. 15, 2018

Related U.S. Application Data

(60) Provisional application No. 62/503,486, filed on May 9, 2017.

(51) Int. Cl.
*A61B 6/00* (2006.01)
*H05G 1/02* (2006.01)
*B66C 19/00* (2006.01)

(52) U.S. Cl.
CPC ............. *H05G 1/02* (2013.01); *A61B 6/4464* (2013.01); *A61B 6/467* (2013.01); *B66C 19/00* (2013.01); *A61B 6/4476* (2013.01)

(58) Field of Classification Search
CPC ..... A61B 6/4464; A61B 6/4476; A61B 6/467; B66C 19/00; H05G 1/02
See application file for complete search history.

(56) References Cited

U.S. PATENT DOCUMENTS

| | | | | |
|---|---|---|---|---|
| 5,572,567 | A * | 11/1996 | Khutoryansky | A61B 6/4283 378/177 |
| 2003/0068008 | A1* | 4/2003 | Schmitt | A61B 6/4464 378/55 |
| 2006/0083353 | A1* | 4/2006 | Boomgaarden | A61B 6/4464 378/196 |
| 2011/0069812 | A1* | 3/2011 | Takahashi | A61B 6/025 378/21 |
| 2013/0121477 | A1* | 5/2013 | Lee | H05G 1/02 378/198 |
| 2015/0124940 | A1* | 5/2015 | Kim | A61B 6/547 378/189 |
| 2016/0220215 | A1* | 8/2016 | Kwak | A61B 6/54 |
| 2016/0256124 | A1* | 9/2016 | Jang | F16M 11/28 |
| 2017/0164914 | A1* | 6/2017 | Kravis | A61B 6/145 |

* cited by examiner

*Primary Examiner* — Mark R Gaworecki

(57) ABSTRACT

An x-ray system mounted on a surface includes a movable x-ray source and a mechanism for moving the x-ray source in at least two transverse directions. The two transverse directions are marked by visually distinguishable indicators. A control panel controls movement of the x-ray source along the transverse directions and includes corresponding markings on control buttons matching the visually distinguishable indicators.

18 Claims, 2 Drawing Sheets

OVERHEAD TUBE CRANE GUIDE

CROSS REFERENCE TO RELATED APPLICATIONS

This application claims priority to U.S. patent application Ser. No. 62/503,486, filed May 9, 2017, in the name of Anthony J. Blasio, and entitled CODING THE DIRECTION OF REMOTE OVERHEAD TUBE CRANE MOVEMENT, which is hereby incorporated by reference herein in its entirety.

BACKGROUND OF THE INVENTION

The subject matter disclosed herein relates to methods and apparatuses for operator control over x-ray system movement.

BRIEF DESCRIPTION OF THE INVENTION

An x-ray system mounted on a surface includes a movable x-ray source and a mechanism for moving the x-ray source in at least two transverse directions. The two transverse directions may each include a marking that is visually distinguishable. The two transverse directions may also each include an end point marked by a visually distinguishable marking near the end point. A control panel controls movement of the x-ray source along the transverse directions and includes markings visually matching the visually distinguishable markings. The control panel may include a hand held remote controller.

In one embodiment, an x-ray system is mounted on a surface, such as a ceiling, and has a movable x-ray source. A motorized carriage is provided for moving the x-ray source in at least two transverse dimensions along rails mounted on the surface. Visually distinguishable indicators are positioned proximate to each of the transverse dimensions for easy recognition. A control panel used for controlling movement of the x-ray source along the two transverse dimensions includes markings visually matching the visually distinguishable indicators, such as having matching colors, shapes, or writing on control buttons or on a control screen.

In another embodiment, a method of controlling movement of an x-ray source in an x-ray system mounted on a surface includes demarcating each movement direction on the mounting surface using visually distinguishable indicators such as colors, shapes, writings, or other markings. Similarly, a remote controller having matching versions of the visually distinguishable indicators is used to control movement of the x-ray source in a desired direction by activating a selected control option that is demarcated using a matching versions of one of the visually distinguishable indicators. In response to the activation, the system is configured to move the x-ray source in the direction indicated by the demarcated control option.

In another embodiment, an x-ray system is mounted on a surface and has a movable x-ray source. A mechanism moves the x-ray source in at least two transverse directions having terminal end points. Visually distinguishable indicators are positioned proximate the terminal end points and a remote controller having markings on corresponding buttons matching the visually distinguishable indicators can be used to move the x-ray source in a desired direction.

This brief description of the invention is intended only to provide a brief overview of subject matter disclosed herein according to one or more illustrative embodiments, and does not serve as a guide to interpreting the claims or to define or limit the scope of the invention, which is defined only by the appended claims. This brief description is provided to introduce an illustrative selection of concepts in a simplified form that are further described below in the detailed description. This brief description is not intended to identify key features or essential features of the claimed subject matter, nor is it intended to be used as an aid in determining the scope of the claimed subject matter. The claimed subject matter is not limited to implementations that solve any or all disadvantages noted in the background.

BRIEF DESCRIPTION OF THE DRAWINGS

So that the manner in which the features of the invention can be understood, a detailed description of the invention may be had by reference to certain embodiments, some of which are illustrated in the accompanying drawings. It is to be noted, however, that the drawings illustrate only certain embodiments of this invention and are therefore not to be considered limiting of its scope, for the scope of the invention encompasses other equally effective embodiments. The drawings are not necessarily to scale, emphasis generally being placed upon illustrating the features of certain embodiments of the invention. In the drawings, like numerals are used to indicate like parts throughout the various views. Thus, for further understanding of the invention, reference can be made to the following detailed description, read in connection with the drawings in which.

DETAILED DESCRIPTION OF THE INVENTION

Figure 1:
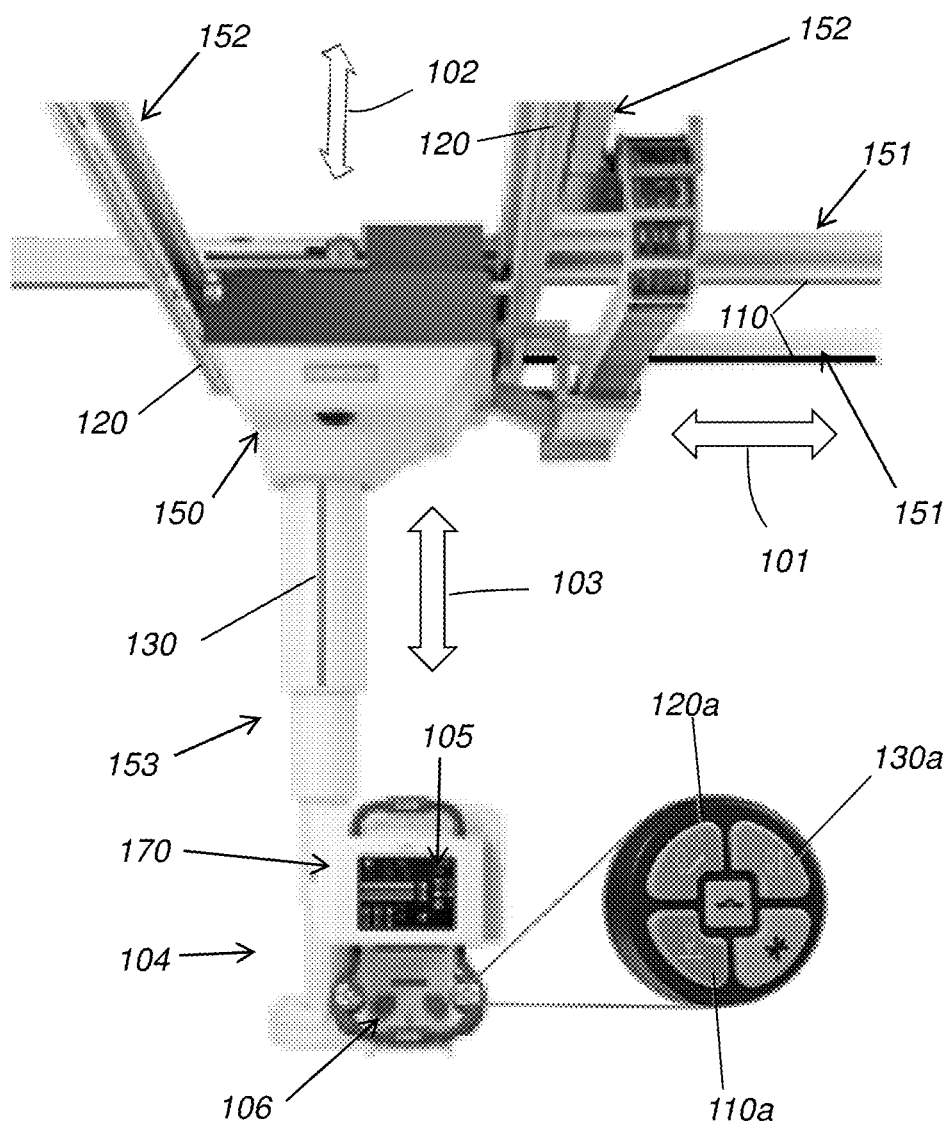
FIG. 1 is a perspective view of a surface mounted x-ray system including a tube crane, a control panel attached thereto, and a control panel on a corresponding hand held remote controller.

With reference to FIG. 1, an x-ray system 100 is shown as it would appear when the x-ray system 100 is mounted on a ceiling. A conventional tube crane assembly may include a carriage 150 and transversely mounted pairs of parallel rails 151, 152, configured to support and transport the carriage 150 as it rides along the rails 151, 152, back and forth in either or both of dimensions 101, 102. The rails 151, 152, are mounted transversely relative to each other along corresponding dimensions 101, 102, which dimensions may be referred to herein as orthogonal x, y coordinate axes, respectively. The carriage 150 may be moved back and forth independently in either or both dimensions 101, 102, typically in a plane that is parallel to a plane of the surface upon which the tube crane assembly is mounted, such as upon a surface of a ceiling in a medical facility. In one embodiment, the ceiling rails 151, 152, run perpendicular to one another and a position of the carriage 150 may be sensed and recorded in a control system 170 of the x-ray system 100 using x, y coordinates corresponding to the dimensions 101, 102, for the tube crane assembly. The conventional tube crane assembly may also include a telescoping column 153 that is raised and lowered along a dimension 103 that is orthogonal to a plane of the x, y coordinate axes, which dimension 103 may be referred to herein as a z axis. Thus, any two of the x, y, z axes may be said to define a plane which is orthogonal to a remaining one of the x, y, z axes. A tube head 104 containing an x-ray source of the x-ray system 100 may be connected to a lower end of the telescoping column 153. As described herein, the lower end of the telescoping column 153 may include a tube head 104 having an x-ray source, a control system 170 having a control screen 105, and/or a manual control panel 106 for input/output communication as between an operator and the x-ray system 100. In some systems, the control screen 105 may include touch sensitive control areas for operator input of commands and instructions for controlling movement of the x-ray source along the x, y, z coordinate axes. In some tube crane assemblies, the carriage 150 is motorized and its movement along the x, y coordinate axes together with a vertical movement of the column 153 along the z axis is controlled using the a manual control panel 106 mounted on the column 153 or tube head 101. Movement of the carriage 150 and column 153 may also be controlled using a remote hand held controller 107, described herein.

To assist an operator of the x-ray system 100 to easily recognize which areas on the control screen 105, which buttons on the control panel 106, or which buttons on the remote controller 107 control a direction of movement of the carriage 150 along dimensions 101, 102 on the rails 151, 152, and the column 153 are configured with strips 110, 120, 130, having different colors. The strips 110, 120, 130, may be comprised of permanent coloring, such as permanent materials of different colors embedded in the surface to which they are applied, a permanent coating applied to the corresponding surface, or they may include temporary interchangeable adhesive colored strips, or other suitable means of visually distinguishable marking. The strips 110, 120, 130, may also include lighted colored optical fibers illuminated by LEDs, or translucent tubes illuminated by one or more colored LED sources. Each of the colors may correspond to one of the xyz axes of movement along dimensions 101, 102, 103. The different colors of these strips 110, 120, 130, may be selected to match colors on the buttons 110a, 120a, 130a, respectively, positioned on the control panel 106 to control movement of the carriage 150 along a direction corresponding thereto. The buttons 110a, 120a, 130a, may include rocker buttons that tilt toward either opposite end of the buttons to select directional movement of the carriage 150 along the rails 151, 152, or vertical movement of the column 153. Similarly, the buttons 110b, 120b, 130b, on the hand held controller 107 include pairs of colored buttons corresponding to the colors of the strips 110, 120, 130, respectively, to select directional movement of the carriage 150 along the rails 151, 152, or vertical movement of the column 153, corresponding thereto. The rail 151, used for supporting the carriage 150 in its movement along the x dimension 101 may have a blue colored strip 110, for example, matching the color of control buttons 110a, 110b; the rail 152, used for supporting the carriage 150 in its movement along the y dimension 102 may have a green colored strip 120, for example, matching the color of control buttons 120a, 120b; and the telescoping column 153, used for supporting the tube head 104 in its vertical movement along the z dimension 103 may have an orange colored strip 130, for example, matching the color of control buttons 130a, 130b. These buttons 110a, 110b, 120a, 120b, are configured to allow simple operator control over motorized movement of the carriage 150 along the set of rails 151, 152, while the buttons 130a, 130b, are configured to allow operator control over a motorized vertical extension of the column 153. Although not described in detail herein above, the screen 105 may also include touch sensitive areas thereon that are color coded in a manner similar to the buttons 110b, 120b, 130b, to provide similar operator control over movements of the carriage 150 and the column 153.

Figure 2:
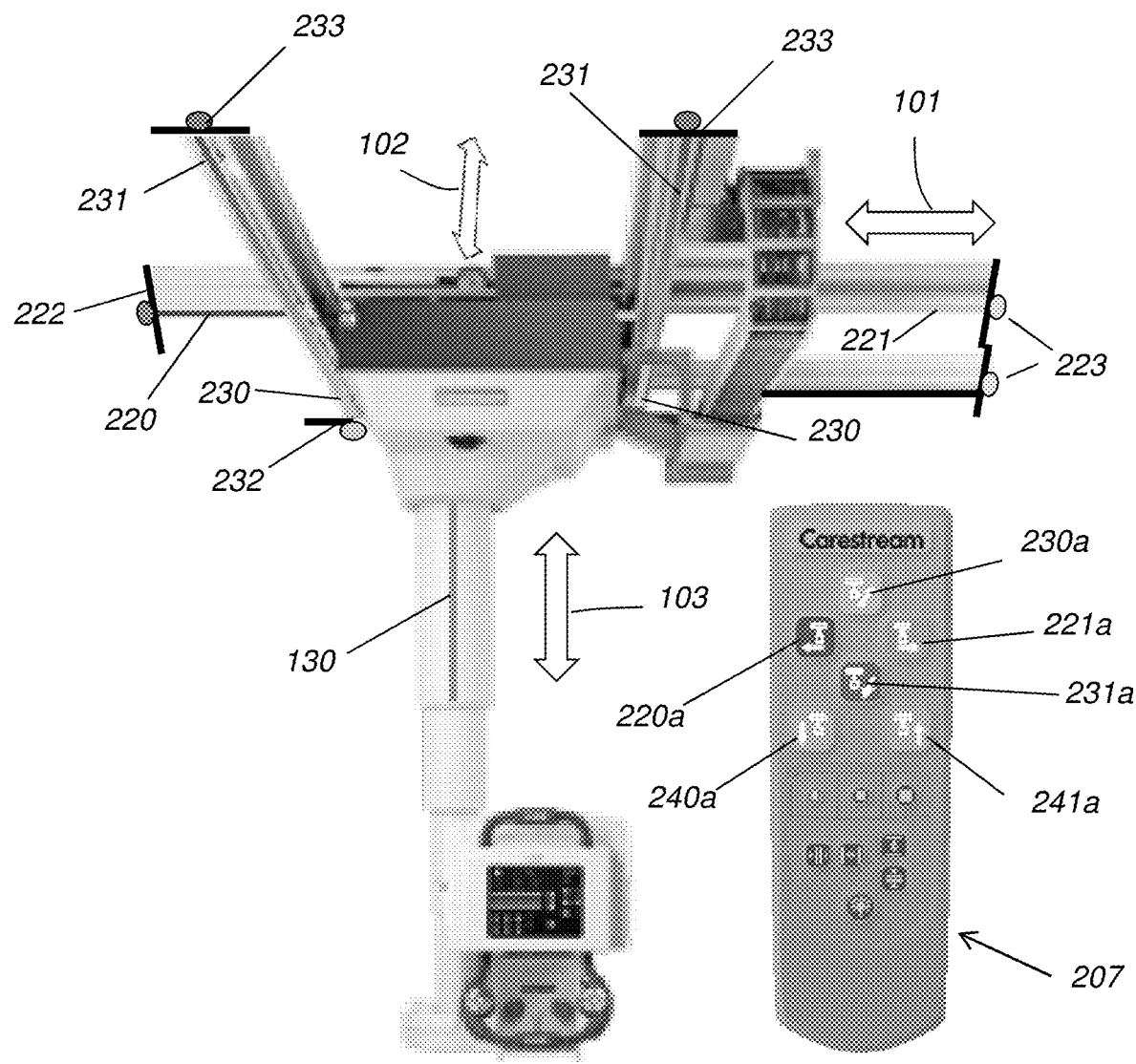
FIG. 2 is another perspective view of a surface mounted x-ray system including a corresponding hand held remote controller.

In one embodiment, the hand held remote controller 107 may be used to initiate motion in each of the dimensions 101, 102, 103. The remote controller 107 is provided with buttons 110b, 120b, 130b, corresponding to three different colors, respectively, to move the tube head 104 in each of three different dimensions 101, 102, 103, along a given axis x, y, z, respectively. In a further, different embodiment, the colored strips 110, 120, 130, on the rails 151, 152, and on the column 153, may be further modified, as illustrated in the x-ray system 200 of FIG. 2. To visibly differentiate one end 220 from another end 221 of the strip 110 corresponding to the rail, or rails, 151 in the x directions 101, for example, the strip 110 may include a darker shade of blue proximate the end 220 and a lighter shade of blue proximate the end 221 of the strip 110. Similarly, to visibly differentiate one end 230 from another end 231 of the strip 120 corresponding to the rail, or rails, 152 in the y directions 102, for example, the strip 120 may include a darker shade of green proximate the end 231 and a lighter shade of green proximate the end 230 of the strip 120. One method of differentiating the ends of the colored strips 110, 120, may include using a color transition of the colored strips 110, 120, such that a dark shade of blue, for example, may be used near one end 220 of a rail, or rails, 151 which transitions along the length of the rail 151 to a light shade of blue at an opposite end 221 of the rail, or rails, 151.

In one embodiment, a means and method of differentiating the terminal ends of the directions 101, 102, may include using terminal end markings with or without strips 110, 120, along the length of the rails 151, 152. At one end of the rail 151, a terminal end marking 222 may include a dark shade of blue, for example, positioned proximate one end 220 of a rail, or rails, 151, on the mounting surface, for example. Similarly, terminal end markings 223 may include a light shade of blue positioned proximate an opposite end 221 of a rail, or rails, 151, on the mounting surface. Similarly, a dark shade of green may be used on terminal end markings 233 proximate one end 231 of a rail, or rails, 152, on the mounting surface, for example. Terminal end markings 232 may use a light shade of green positioned proximate an opposite end 230 of a rail, or rails, 152, on the mounting surface. Therefore, the buttons on the remote controller 207 may then be color coded to match the colors of the markings on terminal ends of the dimensions 101, 102. Thus, the color of button 220a matches the color of the strip 110 at one end 220 of the rail, or rails, 151, or the color of the terminal marking 222, while the color of button 221a matches the color of the strip 110 at another end 221 of the rail, or rails, 151, or the color of the terminal marking 223. Similarly, the color of button 230a matches the color of the strip 120 at one end 230 of the rail, or rails, 152, or the color of the terminal marking 232, while the color of button 231a matches the color of the strip 120 at another end 231 of the rail, or rails, 152, or the color of the terminal marking 233. The colors of the buttons 240a, 241a, corresponding to the strip 130 on the column 153 need not be differentiated in this manner because movement along the vertical dimension 103 would not vary with respect to a perspective of an operator moving about an area around the x-ray system 200. Conversely, the modified color coding scheme in relation to the x, y axes illustrated in the x-ray system 200 of FIG. 2 assists in preventing a left-to-right directional confusion as the operator moves around the x-ray system 200 and changes perspective while observing the x-ray system 200.

In this manner, the colors on the rails 151, 152, may mitigate the potential for a usability problem. Regardless of the operator's orientation, a light blue button 221a, for example, on a remote controller 207 will always move the tube head 104 toward the light blue end 221 of the rail, or rails, 151; the dark blue button 220a toward the dark blue end 220 of the rail, or rails, 151; the light green button 230a toward the light green end 230 of the rail, or rails, 152; and the dark green button 231a toward the dark green end 231 of the rail, or rails, 152.

Although not described in detail herein, various alternative embodiments for providing human-visible transitioning indicators corresponding to the rails 151, 152, are disclosed herein. One such embodiment may include unique markings disposed only at the opposite ends of the rails, without using strips 110, 120, such as using different colors, different geometric shapes or icons, or alphanumeric designators, which different designators may be printed on surfaces, embedded in surfaces, adhered to surfaces, or a combination thereof. In addition, such designators may be implemented using electronics such as electronic LEDs having different color outputs, LEDs used to illuminate optical fibers or translucent tubes, or even electronic screens under programmed control to display colors, symbols, or other designators. As described herein, buttons or touch screen areas may be similarly coded to match any such designations used. Various human-visible distinctive properties may be used to indicate opposite ends of the rails 151, 152. The distinctive characteristics may be readable, such as by using different alphanumeric characters, arrows, shapes, or icons, or they may be sensed by an operator such as by using different colors. Corresponding buttons on a control panel would include matching alphanumeric characters, arrows, shapes, icons, or a corresponding indicator matching the indicators at the opposite ends of the rail or rails. In one embodiment, the unique markings need not be placed only at the ends of the rails. For example, an alphabetic or numeric progression may be place on or adjacent to a rail along its length, whereby the terminal values of the alphanumeric progressions may be placed on the buttons of the remote controller 107, 207 to indicate which opposing end of the rails corresponds thereto.

In one embodiment, colored LED light sources may be placed at the opposite ends of the rails. In one embodiment, a series of transitioning color LED light sources may be placed along the length of a rail. In one embodiment, the control panel buttons may include a colored light source, such as an LED, matching a color of the corresponding LED on the rail. In one embodiment, the remote controller 107, 207 may be configured with dual stage buttons such that a partial depression of a selected control button causes the LEDs on a corresponding rail 151, 152 to flash, or otherwise to indicate the selected xy direction, to allow the operator to visually confirm that the correct movement direction 101, 102, is, in fact, selected, and whereby a full depression of the selected button activates the tube crane assembly system 200 to move the tube head 101 in the confirmed direction 101, 102.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal language of the claims.

What is claimed is:

1. An x-ray system mounted on a surface and having a movable x-ray source, the system comprising:
    a first rail assembly attached to the surface;
    a second rail assembly attached to the surface, the first and second rail assemblies each extending along one of two linear transverse directions;
    a carriage attached to the rail assemblies and to the x-ray source for moving the x-ray source along the two linear transverse directions;
    a first elongated colored region disposed proximate to the first rail assembly;
    a second elongated colored region disposed proximate to the second rail assembly and having a different color than the first elongated colored region; and
    a control panel configured to control movement of the carriage along the two linear transverse directions, the control panel comprising:
    a first manually controllable switch having a same color as the first elongated colored region, the first manually controllable switch configured to move the carriage in a direction parallel to the first rail assembly; and
    a second manually controllable switch having a same color as the second elongated colored region, the second manually controllable switch configured to move the carriage in a direction parallel to the second rail assembly.

2. The system of claim 1, wherein the two linear transverse directions are coplanar.

3. The system of claim 2, wherein the two linear transverse directions are orthogonal.

4. The system of claim 3, wherein the two linear transverse directions are coplanar in a plane parallel to a plane of the surface.

5. The system of claim 1, wherein the first and second elongated colored regions and the first and second manually controllable switches' colors are selected to be visually distinguishable by a human operator.

6. The system of claim 1, wherein the first and second elongated colored regions and the first and second manually controllable switches further comprise visually distinguishable alphanumeric characters, geometric shapes or symbols, or a combination thereof.

7. The system of claim 1, wherein the first and second manually controllable switches comprise buttons or areas on a touch screen.

8. The system of claim 7, wherein the first elongated colored region comprises a first plurality of electronic colored light sources, and the second elongated colored region comprises a second plurality of electronic colored light sources having a different color than the first plurality of electronic colored light sources, and wherein the first and second manually controllable switches are configured to activate the first and second plurality of electronic colored light sources, respectively.

9. The system of claim 1, wherein the control panel is disposed on a hand held remote controller.

10. A method of controlling movement of an x-ray source in an x-ray system mounted on a surface, the method comprising:
    demarcating each of a plurality of movement directions including applying an elongated colored strip on the surface for each of the plurality of movement directions, each of the colored strips having a different visually distinguishable color, and each of the colored strips disposed parallel to a corresponding movement direction;

coloring each of a plurality of control buttons on a controller a same color as one of the elongated color strips;

activating a selected one of the control buttons on the controller; and in response to the step of activating, moving the x-ray source in a direction parallel to an elongated strip having a same color as the selected one of the control buttons.

11. An x-ray system mounted on a surface and having a movable x-ray source, the system comprising:

a mechanism for moving the x-ray source in at least two transverse directions, wherein the at least two transverse directions each include two end points;

a plurality of indicators each having a different visually distinguishable color and each positioned proximate to one of the end points; and a controller configured to control the mechanism for moving movement of the x-ray source, the controller comprising a plurality of manually controlled switches for causing the mechanism to move the x-ray source, the plurality of manually controlled switches each having a same color as one of the plurality of indicators, wherein each of the plurality of manually controlled switches is configured to be activated to cause the mechanism to move the x-ray source toward an indicator having the same color as the activated switch.

12. The system of claim 11, wherein the at least two transverse directions are coplanar.

13. The system of claim 12, wherein the at least two transverse directions are orthogonal.

14. The system of claim 13, wherein the at least two transverse directions are coplanar in a plane parallel to a plane of the surface.

15. The system of claim 11, wherein the plurality of indicators comprise visually distinguishable alphanumeric characters, geometric shapes or symbols, or a combination thereof.

16. The system of claim 15, wherein the controller comprises a hand held remote controller.

17. The system of claim 11, wherein the plurality of manually controlled switches comprise of a plurality of buttons or a plurality of areas on a touch screen.

18. The system of claim 17, wherein the plurality of indicators comprise a plurality of electronic light sources, and wherein the plurality of buttons are configured to each activate a corresponding one of the electronic light sources.

* * * * *

UNITED STATES PATENT AND TRADEMARK OFFICE
CERTIFICATE OF CORRECTION

PATENT NO. : 10,709,004 B2
APPLICATION NO. : 15/967963
DATED : July 7, 2020
INVENTOR(S) : Anthony J. Blasio Page 1 of 1

It is certified that error appears in the above-identified patent and that said Letters Patent is hereby corrected as shown below:

Column 7, Line 22   Please replace "moving movement of the x-ray source, the controller" with --moving the x-ray source, the controller--

Signed and Sealed this
Fifteenth Day of September, 2020

Andrei Iancu
*Director of the United States Patent and Trademark Office*